US009763565B2

(12) United States Patent
Homan

(10) Patent No.: US 9,763,565 B2
(45) Date of Patent: Sep. 19, 2017

(54) CAPSULE ENDOSCOPE DEVICE

(71) Applicant: OLYMPUS CORPORATION, Tokyo (JP)

(72) Inventor: Masatoshi Homan, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/993,504

(22) Filed: Jan. 12, 2016

(65) Prior Publication Data

US 2016/0120396 A1     May 5, 2016

Related U.S. Application Data

(63) Continuation of application No. PCT/JP2015/055201, filed on Feb. 24, 2015.

(30) Foreign Application Priority Data

May 26, 2014   (JP) ................................ 2014-108413

(51) Int. Cl.
*A61B 1/00*    (2006.01)
*A61B 1/04*    (2006.01)
(Continued)

(52) U.S. Cl.
CPC .......... *A61B 1/045* (2013.01); *A61B 1/00009* (2013.01); *A61B 1/041* (2013.01); *A61B 1/05* (2013.01)

(58) Field of Classification Search
CPC . A61B 1/041; A61B 1/00009; A61B 1/00036; A61B 2560/0209;
(Continued)

(56) References Cited

U.S. PATENT DOCUMENTS 6,709,387 B1    3/2004  Glukhovsky et al.
7,022,067 B2    4/2006  Glukhovsky et al.
(Continued)

FOREIGN PATENT DOCUMENTS

JP    2004-154176 A    6/2004
JP    2004-521662 A    7/2004
(Continued)

OTHER PUBLICATIONS

Japanese Office Action dated Sep. 8, 2015 issued in JP 2015-532212.

*Primary Examiner* — Alexandra Newton
(74) *Attorney, Agent, or Firm* — Scully, Scott, Murphy & Presser, P.C.

(57) ABSTRACT

A capsule endoscope includes: an imaging unit configured to capture inside of a subject and to generate an image of the inside of the subject; a brightness distribution measurement unit configured to measure a brightness distribution in the image generated by the imaging unit; and an imaging controller configured to switch a frame rate of the imaging unit to a frame rate higher than a reference frame rate when an area having brightness lower than a predetermined value is distributed at a center of the image in the brightness distribution measured by the brightness distribution measurement unit and to switch the frame rate of the imaging unit to a frame rate lower than the reference frame rate when the area having the brightness lower than the predetermined value is distributed outside the center of the image.

4 Claims, 14 Drawing Sheets

(51) Int. Cl.
*A61B 1/045* (2006.01)
*A61B 1/05* (2006.01)

(58) Field of Classification Search
CPC ......... G06T 2207/30028; G06T 7/0012; G06T 2207/10068; G06T 7/403; G06T 2207/20021; G06T 2207/30032; G06T 2207/30092; G06T 7/20
See application file for complete search history.

(56) References Cited

U.S. PATENT DOCUMENTS

| | | |
|---|---|---|
| 7,623,690 B2 | 11/2009 | Cahill et al. |
| 8,005,279 B2 | 8/2011 | Yagi et al. |
| 8,159,549 B2 | 4/2012 | Glukhovsky et al. |
| 8,368,770 B2 | 2/2013 | Glukhovsky et al. |
| 8,626,272 B2 * | 1/2014 | Avni ............... A61B 1/041 600/476 |
| 9,118,817 B2 | 8/2015 | Glukhovsky et al. |
| 9,324,145 B1 * | 4/2016 | Cherevatsky ......... A61B 5/066 |
| 2007/0161858 A1 | 7/2007 | Homan et al. |
| 2009/0192348 A1 | 7/2009 | Nishino |
| 2010/0119133 A1 * | 5/2010 | Glukhovsky ......... A61B 1/041 382/128 |
| 2010/0130818 A1 | 5/2010 | Jung et al. |
| 2011/0184237 A1 | 7/2011 | Homan et al. |
| 2015/0157195 A1 | 6/2015 | Iwaisako |
| 2015/0305605 A1 | 10/2015 | Glukhovsky et al. |

FOREIGN PATENT DOCUMENTS

| | | |
|---|---|---|
| JP | 2009-172287 A | 8/2009 |
| JP | 2010-524557 A | 7/2010 |
| WO | WO 2006/100808 A1 | 9/2006 |
| WO | WO 2014/042096 A1 | 3/2014 |

* cited by examiner

FIG.3

| R | Gr | R | Gr | R | Gr | R | Gr |
|---|----|---|----|---|----|---|----|
| Gb | B | Gb | B | Gb | B | Gb | B |
| R | Gr | R | Gr | R | Gr | R | Gr |
| Gb | B | Gb | B | Gb | B | Gb | B |
| R | Gr | R | Gr | R | Gr | R | Gr |
| Gb | B | Gb | B | Gb | B | Gb | B |
| R | Gr | R | Gr | R | Gr | R | Gr |
| Gb | B | Gb | B | Gb | B | Gb | B |

T1 (upper-left 2×2: R, Gr, Gb, B)
231

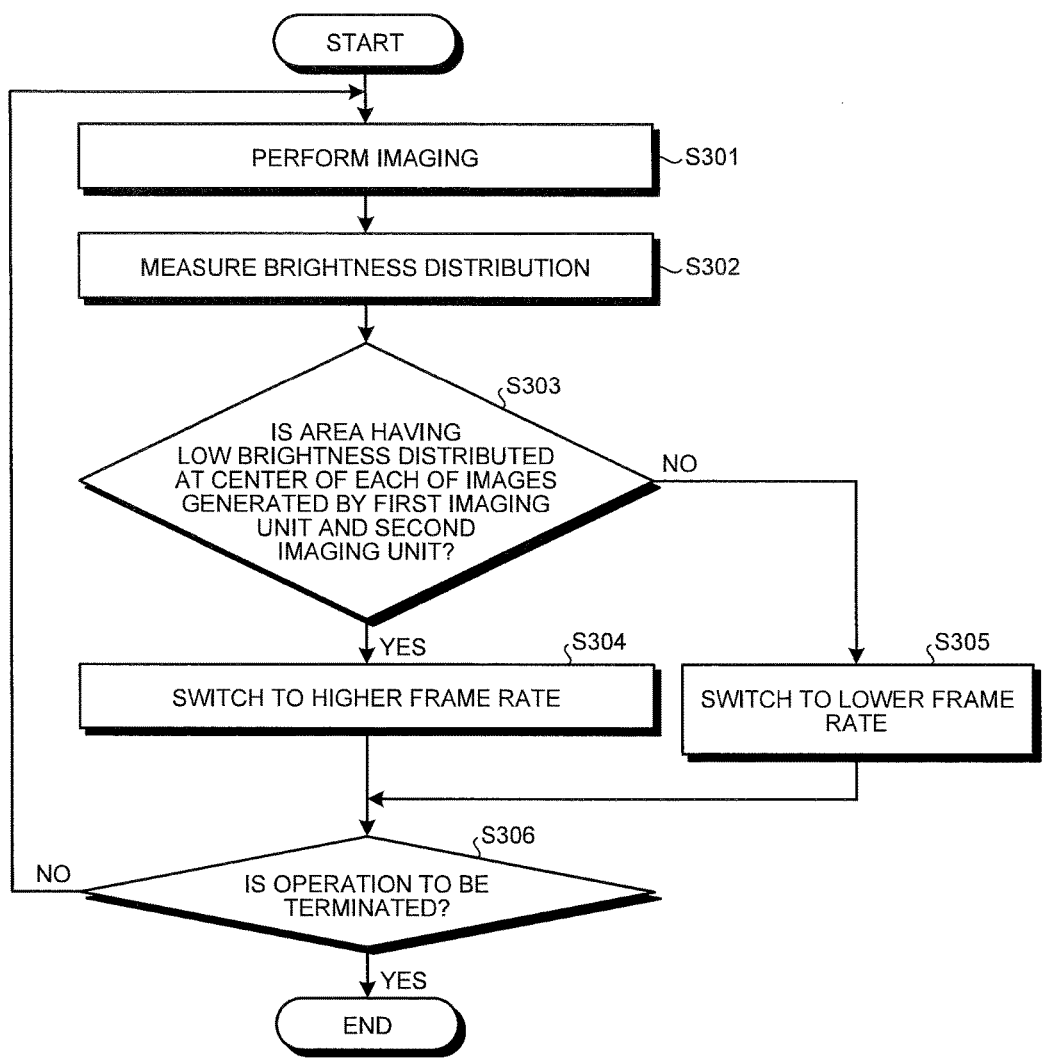

CAPSULE ENDOSCOPE DEVICE

CROSS REFERENCES TO RELATED APPLICATIONS

This application is a continuation of PCT international application Ser. No. PCT/JP2015/055201, filed on Feb. 24, 2015 which designates the United States, incorporated herein by reference, and which claims the benefit of priority from Japanese Patent Applications No. 2014-108413, filed on May 26, 2014, incorporated herein by reference.

BACKGROUND

1. Technical Field

The disclosure relates to a capsule endoscope device that is inserted into a subject, moves within a body cavity of the subject, and acquires information on the subject.

2. Related Art

There has been known in the field of endoscopes a capsule endoscope device incorporating an imaging function, a radio communication function and the like into a capsule-shaped casing formed in the size that is insertable into a digestive tract of a subject such as a patient. The capsule endoscope device is swallowed through the mouth of the subject, generates image data by successively capturing the inside of the subject such as the digestive tract while moving therethrough by peristalsis or the like, and successively transmits the image data by radio communication.

In this type of capsule endoscope device, there is known a technique in which a similarity calculation circuit is provided to calculate similarity between two temporally adjacent images and switch a frame rate of an imaging unit on the basis of a result detected by the circuit in order to save power (refer to Japanese Laid-open Patent Publication No. 2009-172287).

SUMMARY

In some embodiments, a capsule endoscope device is configured to be inserted into a subject. The device includes: an imaging unit configured to capture inside of the subject and to generate an image of the inside of the subject; a brightness distribution measurement unit configured to measure a brightness distribution in the image generated by the imaging unit; and an imaging controller configured to switch a frame rate of the imaging unit to a frame rate higher than a reference frame rate when an area having brightness lower than a predetermined value is distributed at a center of the image in the brightness distribution measured by the brightness distribution measurement unit and to switch the frame rate of the imaging unit to a frame rate lower than the reference frame rate when the area having the brightness lower than the predetermined value is distributed outside the center of the image.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 3 is a diagram schematically illustrating a color filter of an imaging unit in the capsule endoscope device according to the first embodiment of the present invention;

FIG. 12 is a flowchart illustrating an overview of processing executed by the capsule endoscope device according to the third embodiment of the present invention;

DETAILED DESCRIPTION

Embodiments of the present invention will now be described in detail with reference to the drawings. The present invention is not to be limited by the following embodiments. Moreover, each diagram referenced in the following description merely illustrates the shape, size, and positional relationship schematically for one to be able to understand the content of the present invention. That is, the present invention is not to be limited to the shape, size and positional relationship illustrated in each drawing. While there will be illustrated a capsule endoscope system that includes a processing device displaying an in-vivo image of a subject by receiving a radio signal from a capsule endoscope device that is inserted into the subject and captures the in-vivo image of the subject, the present invention is not to be limited by such embodiment. Furthermore, the same configuration will be assigned the same reference signs.

First Embodiment

Schematic Configuration of Capsule Endoscope System

Figure 1:
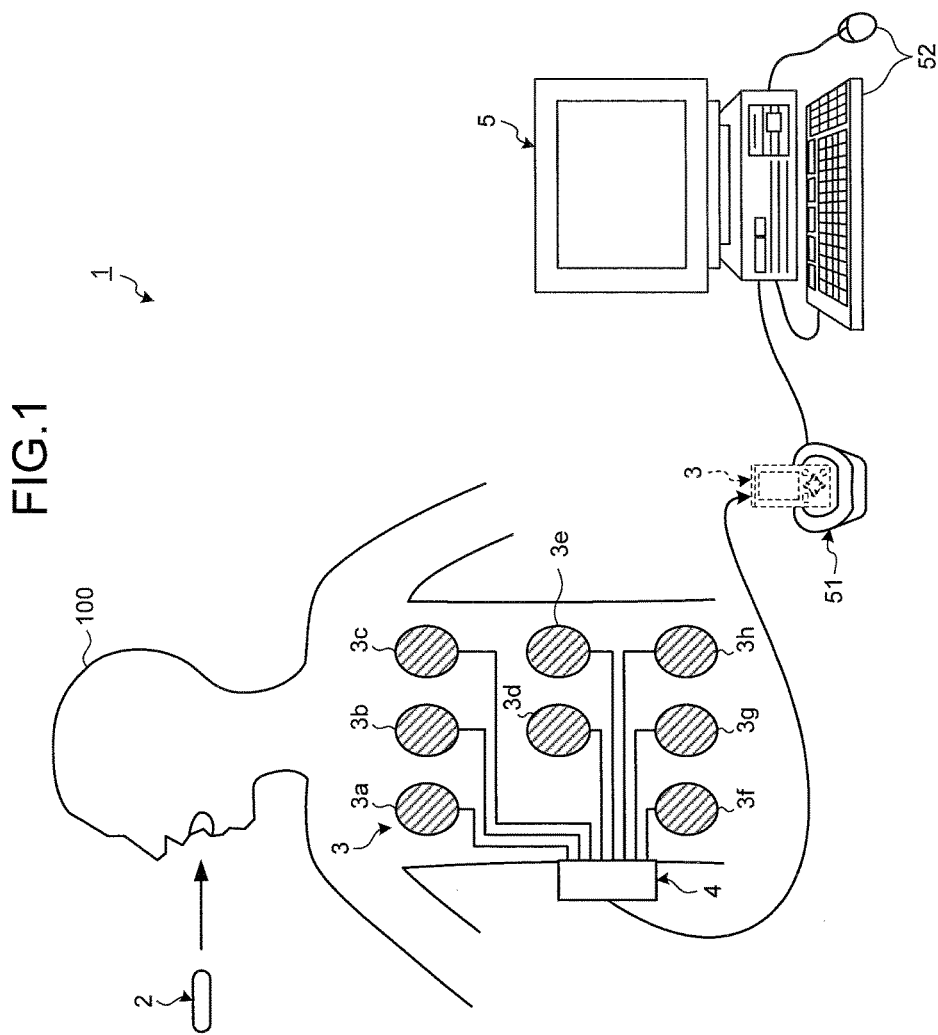
FIG. 1 is a schematic diagram illustrating a schematic configuration of a capsule endoscope system according to a first embodiment of the present invention.

FIG. 1 is a schematic diagram illustrating a schematic configuration of a capsule endoscope system according to a first embodiment of the present invention.

A capsule endoscope system 1 illustrated in FIG. 1 includes a capsule endoscope device 2 that captures an in-vivo image inside a subject 100, a receiving antenna unit 3 that receives a radio signal transmitted from the capsule endoscope device 2 inserted into the subject 100, a receiving device 4 where the receiving antenna unit 3 is detachably connected to and that performs predetermined processing on the radio signal received by the receiving antenna unit 3 to record or display the signal, and an image processing apparatus 5 that processes and/or displays an image corresponding to image data of the inside of the subject 100 captured by the capsule endoscope device 2.

The capsule endoscope device 2 has an imaging function that captures the inside of the subject 100 and a radio communication function that transmits in-vivo information containing image data acquired by capturing the inside of the subject 100 to the receiving antenna unit 3. The capsule endoscope device 2 is swallowed into the subject 100, passes through an esophagus inside the subject 100, and moves through a body cavity of the subject 100 by peristalsis of a lumen of a digestive tract. The capsule endoscope device 2 successively captures the inside of the body cavity of the subject 100 at a small time interval such as 0.5 seconds (2 fps) while moving through the body cavity of the subject 100, generates image data of the inside of the subject 100 being captured, and successively transmits the image data to the receiving antenna unit 3. The detailed configuration of the capsule endoscope device 2 will be described later.

The receiving antenna unit 3 includes receiving antennas 3a to 3h. The receiving antennas 3a to 3h receive the radio signal from the capsule endoscope device 2 and transmit it to the receiving device 4. Each of the receiving antennas 3a to 3h is formed of a loop antenna and arranged at a predetermined position on the outer surface of the subject 100, the predetermined position corresponding to each organ inside the subject 100 through which the capsule endoscope device 2 passes, for example.

The receiving device 4 records the image data of the inside of the subject 100 included in the radio signal transmitted from the capsule endoscope device 2 through the receiving antennas 3a to 3h, or displays an image corresponding to the image data of the inside of the subject 100. The receiving device 4 records position information of the capsule endoscope device 2 as well as time information indicating time in association with the image data received through the receiving antennas 3a to 3h. The receiving device 4 is housed in a receiving device holder (not illustrated) and carried on the subject 100 while the capsule endoscope device 2 performs an examination, such as while the device is inserted through the mouth of the subject 100, passes through the digestive tract, and is excreted from the subject 100. After the capsule endoscope device 2 completes the examination, the receiving device 4 is removed from the subject 100 and connected to the image processing apparatus 5 to transfer thereto the image data or the like received from the capsule endoscope device 2.

The image processing apparatus 5 displays an image corresponding to the image data of the inside of the subject 100 acquired through the receiving device 4. The image processing apparatus 5 includes a cradle 51 that reads the image data or the like from the receiving device 4 and an operation input device 52 such as a keyboard and a mouse. The cradle 51 acquires the image data from the receiving device 4 as well as associated information associated with the image data such as position information, time information and identification information of the capsule endoscope device 2 when the receiving device 4 is mounted to the cradle, and transfers the various pieces of information being acquired to the image processing apparatus 5. The operation input device 52 accepts input by a user. The user operates the operation input device 52 to observe a biological region inside the subject 100 such as an esophagus, a stomach, a small intestine and a large intestine while looking at an image of the inside of the subject 100 successively displayed by the image processing apparatus 5, and then diagnoses the subject 100.

Configuration of Capsule Endoscope Device

Figure 2:
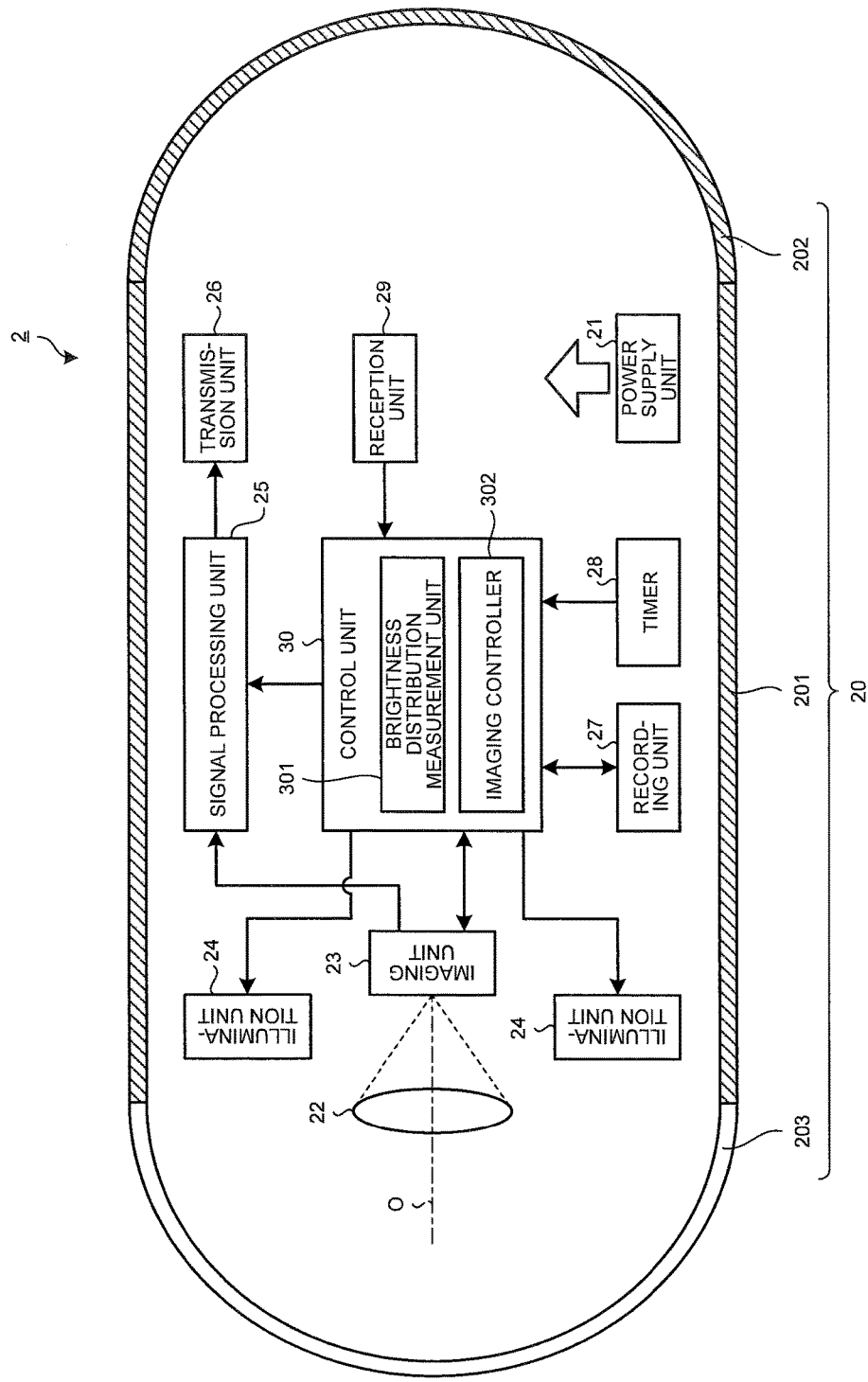
FIG. 2 is a block diagram illustrating a functional configuration of a capsule endoscope device according to the first embodiment of the present invention.

The detailed configuration of the capsule endoscope device 2 described with reference to FIG. 1 will now be described. FIG. 2 is a block diagram illustrating a functional configuration of the capsule endoscope device 2.

The capsule endoscope device 2 illustrated in FIG. 2 includes a casing 20, a power supply unit 21, an optical system 22, an imaging unit 23, an illumination unit 24, a signal processing unit 25, a transmission unit 26, a recording unit 27, a timer 28, a reception unit 29, and a control unit 30.

The casing 20 is capsule-shaped and sized to be easily inserted into the subject 100. The casing 20 has a cylindrical portion 201, and dome-shaped dome portions 202 and 203 that close openings at both ends of the cylindrical portion 201. Each of the cylindrical portion 201 and the dome portion 202 is formed by using an opaque, colored member shielding visible light. The dome portion 203 is formed by using an optical member that can transmit light in a predetermined wavelength band such as the visible light. The casing 20 formed of the cylindrical portion 201 and the dome portions 202 and 203 accommodates the power supply unit 21, the optical system 22, the imaging unit 23, the illumination unit 24, the signal processing unit 25, the transmission unit 26, the recording unit 27, the timer 28, the reception unit 29, and the control unit 30 as illustrated in FIG. 2.

The power supply unit 21 supplies power to each unit in the capsule endoscope device 2. The power supply unit 21 is formed by using a primary or secondary battery such as a button battery, and a power supply circuit boosting the power supplied from the button battery. The power supply unit 21 further includes a magnetic switch that switches on/off the power supply by a magnetic field that is externally applied.

The optical system 22 is formed by using a plurality of lenses and forms a subject image by condensing reflected light of illumination light radiated by the illumination unit 24 onto an imaging surface of the imaging unit 23. The optical system 22 is arranged in the casing 20 such that an optical axis of the system corresponds with a central axis O of the casing 20 in a longitudinal direction.

Under control of the control unit 30, the imaging unit 23 generates image data of the subject 100 by performing photoelectric conversion on the subject image formed on a light receiving surface by the optical system 22. Specifically, the imaging unit 23 captures the subject 100 at a reference frame rate such as 4 fps under control of the control unit 30 and generates the image data of the subject 100. The imaging unit 23 is formed by using an imaging element such as a CCD (Charge Coupled Device) or a CMOS (Complementary Metal Oxide Semiconductor) that is formed of a plurality of pixels arrayed in two dimensions and a color filter laminated on each of the plurality of pixels.

FIG. 3 is a diagram schematically illustrating a color filter 231 of the imaging unit 23. As illustrated in FIG. 3, the color filter 231 is formed by using a color filter in Bayer array in which a filter Gr, a filter Gb, a filter R and a filter B form one set T1. Moreover, the imaging unit 23 is arranged in the casing 20 such that the light receiving surface of the imaging unit 23 is orthogonal to the central axis O.

Under control of the control unit 30, the illumination unit 24 radiates the illumination light toward a subject within an imaging field of the imaging unit 23 in synchronization with the frame rate of the imaging unit 23. Moreover, under control of the control unit 30, the illumination unit 24 radiates the illumination light toward the subject within the imaging field of the imaging unit 23 with predetermined intensity. The illumination unit 24 is formed by using an LED (Light Emitting Diode) and a drive circuit or the like.

The signal processing unit 25 performs predetermined image processing on the image data input from the imaging unit 23 and outputs the data to the transmission unit 26. The predetermined image processing in this case is noise reduction processing or gain up processing, for example.

The transmission unit 26 wirelessly transmits the image data successively input from the signal processing unit 25 to the outside. The transmission unit 26 is formed by using a transmitting antenna and a modulation circuit that modulates the image data into a radio signal by performing signal processing such as modulation.

The recording unit 27 records a program indicating various operations executed by the capsule endoscope device 2 as well as identification information identifying the capsule endoscope device 2.

The timer 28 has a timing function. The timer 28 outputs timing data to the control unit 30.

The reception unit 29 receives the radio signal transmitted from the outside and outputs it to the control unit 30. The reception unit 29 is formed by using a receiving antenna and a demodulation circuit that performs signal processing such as demodulation on the radio signal and outputs the signal to the control unit 30.

The control unit 30 controls an operation of each unit in the capsule endoscope device 2. The control unit 30 is formed by using a CPU (Central Processing Unit). The control unit 30 includes a brightness distribution measurement unit 301 and an imaging controller 302.

The brightness distribution measurement unit 301 measures a brightness distribution of an image corresponding to the image data generated by the imaging unit 23.

The imaging controller 302 switches the frame rate of the imaging unit 23 on the basis of the brightness distribution of the image measured by the brightness distribution measurement unit 301. Specifically, the imaging controller 302 switches the frame rate of the imaging unit 23 to a frame rate higher than the reference frame rate when an area having brightness lower than a predetermined value is distributed at the center of the image in the brightness distribution measured by the brightness distribution measurement unit 301 and, on the other hand, switches the frame rate of the imaging unit 23 to a frame rate lower than the reference frame rate when the area having brightness lower than the predetermined value is distributed outside the center of the image. The imaging controller 302 for example switches the frame rate of the imaging unit 23 from 4 fps to 8 fps when the area having the brightness lower than the predetermined value is distributed at the center of the image in the brightness distribution measured by the brightness distribution measurement unit 301 and, on the other hand, switches the frame rate of the imaging unit 23 from 4 fps to 2 fps when the area having the brightness lower than the predetermined value is distributed outside the center of the image. Here, the predetermined value equals 0.3 assuming a full scale of the brightness is 1. The imaging controller 302 also adjusts the intensity of the illumination light radiated from the illumination unit 24 on the basis of the brightness distribution of the image measured by the brightness distribution measurement unit 301.

Processing Executed by Capsule Endoscope Device

Figure 4:
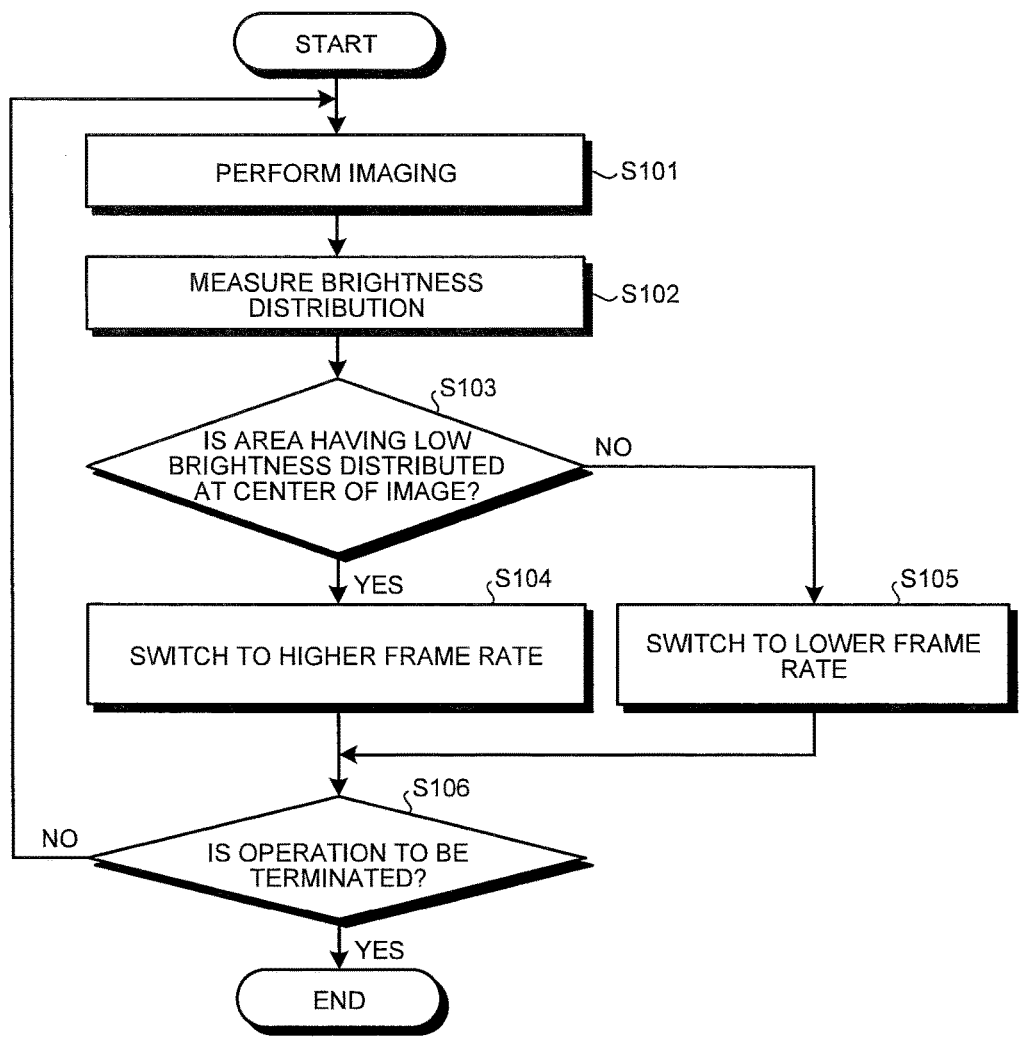
FIG. 4 is a flowchart illustrating an overview of processing executed by the capsule endoscope device according to the first embodiment of the present invention.

Processing executed by the aforementioned capsule endoscope device 2 will now be described. FIG. 4 is a flowchart illustrating an overview of the processing executed by the capsule endoscope device 2.

As illustrated in FIG. 4, the imaging unit 23 first captures an imaging area irradiated with the illumination light by the illumination unit 24 (step S101).

The brightness distribution measurement unit 301 then measures the brightness distribution of the image corresponding to the image data generated by the imaging unit 23 (step S102).

After that, the imaging controller 302 determines whether or not the area having the brightness lower than the predetermined value is distributed at the center of the image, on the basis of a measurement result measured by the brightness distribution measurement unit 301 (step S103). When the imaging controller 302 determines that the area having the low brightness is distributed at the center of the image (step S103: Yes), the imaging controller 302 switches the frame rate of the imaging unit 23 to a higher frame rate (from 4 fps to 8 fps) that is higher than the reference frame rate (step S104). Following step S104, the capsule endoscope device 2 proceeds to step S106 to be described.

When the imaging controller 302 determines in step S103 that the area having the brightness lower than the predetermined value is not distributed at the center of the image (step S103: No), the imaging controller 302 switches the frame rate of the imaging unit 23 to a lower frame rate (from 4 fps to 2 fps) that is lower than the reference frame rate (step S105). Following step S105, the capsule endoscope device 2 proceeds to step S106 to be described.

There will now be described a switching method in which the imaging controller 302 switches the frame rate of the imaging unit 23.

Figure 5A:
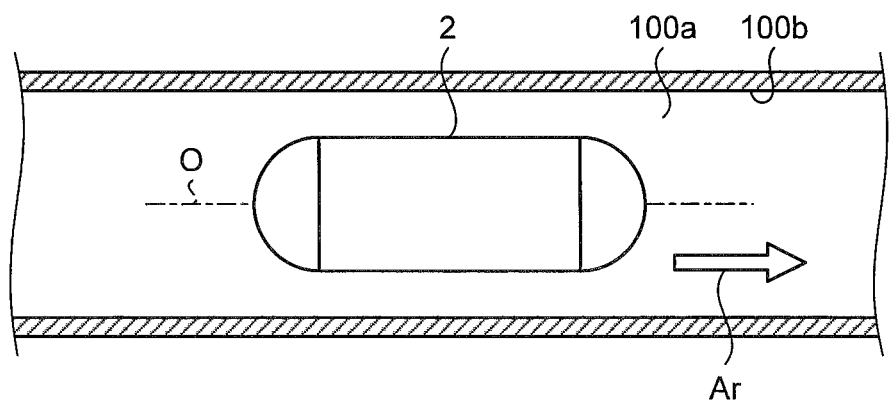
FIG. 5A is a diagram illustrating an example of a state of a capsule endoscope inside a lumen of a subject.
Figure 5B:
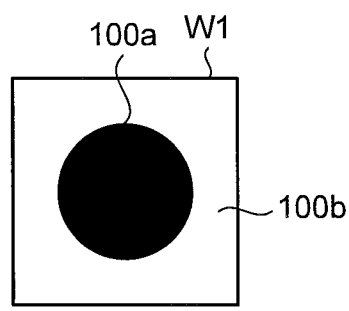
FIG. 5B is a diagram illustrating an image corresponding to image data captured by the imaging unit under the condition illustrated in FIG. 5A.
Figure 6A:
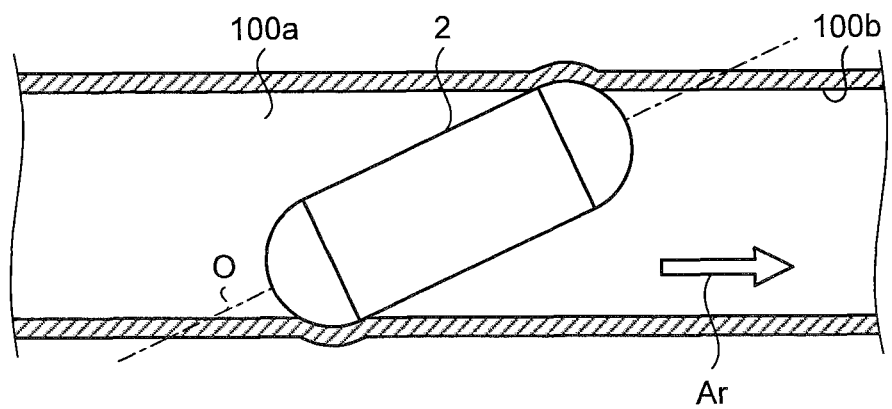
FIG. 6A is a diagram illustrating an example of another state of the capsule endoscope device inside the lumen of the subject.
Figure 6B:
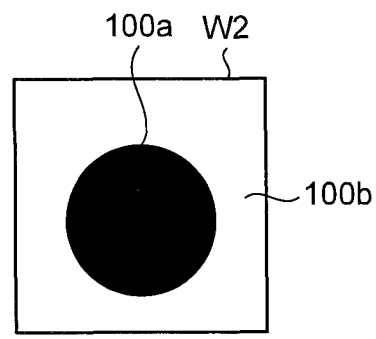
FIG. 6B is a diagram illustrating an image corresponding to image data captured by the imaging unit under the condition illustrated in FIG. 6A.
Figure 7A:
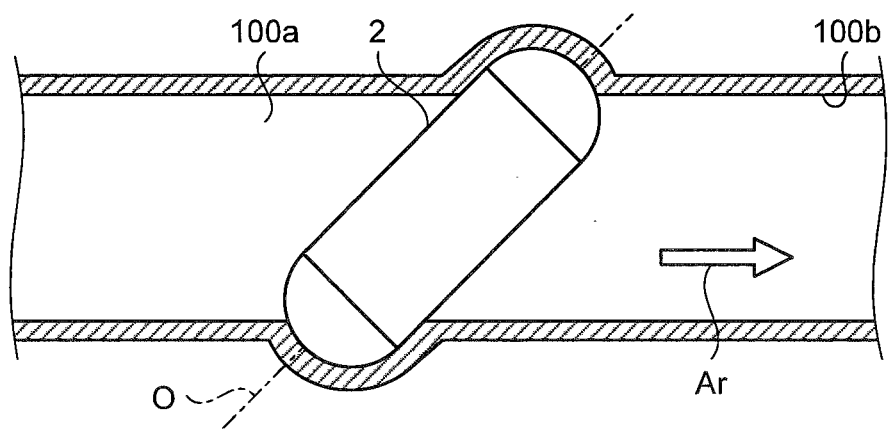
FIG. 7A is a diagram illustrating an example of another state of the capsule endoscope device inside the lumen of the subject.
Figure 7B:
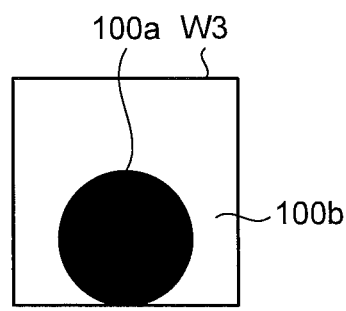
FIG. 7B is a diagram illustrating an image corresponding to image data captured by the imaging unit under the condition illustrated in FIG. 7A.

FIG. 5A is a diagram illustrating an example of a state (first state) of the capsule endoscope device 2 inside a lumen of the subject 100. FIG. 5B is a diagram illustrating an image corresponding to image data captured by the imaging unit 23 under the condition illustrated in FIG. 5A. FIG. 6A is a diagram illustrating an example of another state (second state) of the capsule endoscope device 2 inside the lumen of the subject 100. FIG. 6B is a diagram illustrating an image corresponding to image data captured by the imaging unit 23 under the condition illustrated in FIG. 6A. FIG. 7A is a diagram illustrating an example of another state (third state) of the capsule endoscope device 2 inside the lumen of the subject 100. FIG. 7B is a diagram illustrating an image corresponding to image data captured by the imaging unit 23 under the condition illustrated in FIG. 7A.

As illustrated in FIG. 5A, the capsule endoscope device 2 is not in contact with the lumen when the central axis O of the capsule endoscope device 2 is oriented in a lumen orientation (arrow Ar) of the subject 100, so that the capsule endoscope device moves faster through the lumen with no friction generated. As a result, the capsule endoscope device 2 has more information on the lumen that cannot be imaged when the frame rate of the imaging unit 23 (such as 2 fps) is lower than the reference frame rate (such as 4 fps), but has less information on the lumen that cannot be imaged when the frame rate of the imaging unit 23 (such as 8 fps) is higher than the reference frame rate.

On the other hand, as illustrated in FIGS. 6A and 7A, the capsule endoscope device 2 is in contact with the lumen when the central axis O of the capsule endoscope device 2 is at an angle with respect to the lumen orientation (arrow Ar) of the subject 100, so that the capsule endoscope device moves slower through the lumen due to friction. As a result, the capsule endoscope device 2 ends up imaging the same information on the lumen when the frame rate of the imaging unit 23 is higher than the reference frame rate, and has no information on the lumen that cannot be imaged even when the frame rate of the imaging unit 23 is lower than the reference frame rate.

The capsule endoscope device 2 images W1 to W3 illustrated in FIGS. 5B, 6B and 7B under the conditions illustrated in FIGS. 5A, 6A and 7A, respectively. Each of the images W1 to W3 includes a lumen 100a and a lumen inner wall 100b. The lumen 100a receives less reflection of the illumination light radiated by the illumination unit 24 and thus has lower brightness than the surrounding lumen inner wall 100b, for example. Specifically, the brightness of the lumen 100a is nearly zero.

The capsule endoscope device 2 moves faster through the lumen when the central axis O of the capsule endoscope device 2 corresponds with the center of the lumen, whereby a distance the capsule endoscope device 2 travels through the lumen per unit time increases. On the other hand, the capsule endoscope device 2 moves slower per unit time through the lumen when the central axis O of the capsule endoscope device 2 does not correspond with the center of the lumen. In other words, the distance the capsule endoscope device 2 travels through the lumen per unit time is determined according to the orientation of the lumen imaged by the capsule endoscope device 2 (first condition).

Moreover, an amount of information on the lumen that can be acquired by the capsule endoscope device 2 per unit time increases as the distance the capsule endoscope device 2 travels through the lumen per unit time increases (second condition).

Furthermore, the amount of information on the lumen that can be acquired by the capsule endoscope device 2 per unit time increases as the frame rate of the imaging unit 23 in the capsule endoscope device 2 is higher (third condition).

Therefore, on the basis of the first to third conditions, the frame rate of the imaging unit 23 in the capsule endoscope device 2 is set according to the orientation of the lumen imaged by the capsule endoscope device 2.

Accordingly, in the first embodiment, the imaging controller 302 switches the frame rate of the imaging unit 23 on the basis of the brightness distribution measured by the brightness distribution measurement unit 301 in the image corresponding to the image data generated by the imaging unit 23. That is, on the basis of the brightness distribution of the image measured by the brightness distribution measurement unit 301, the imaging controller 302 determines a position of the lumen 100a that is the area having lower brightness than the surrounding area within the image corresponding to the image data generated by the imaging unit 23, and then switches the frame rate of the imaging unit 23 on the basis of the determination result and the position within the image.

Figure 8:
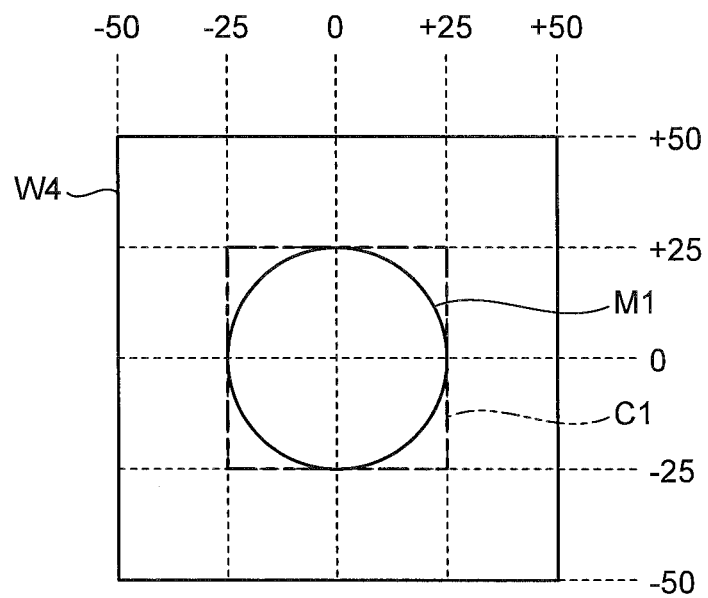
FIG. 8 is a diagram schematically illustrating an overview of a determination method in which an imaging controller of the capsule endoscope device according to the first embodiment of the present invention determines a position of the lumen in an image on the basis of a brightness distribution measured by a brightness distribution measurement unit.

There will now be described a determination method in which the imaging controller 302 determines the position of the lumen within the image on the basis of the brightness distribution measured by the brightness distribution measurement unit 301. FIG. 8 is a diagram schematically illustrating an overview of the determination method in which the imaging controller 302 determines the position of the lumen within the image on the basis of the brightness distribution measured by the brightness distribution measurement unit 301. It is assumed as illustrated in FIG. 8 that a whole image for which the brightness is calculated by the brightness distribution measurement unit 301 ranges from −50 to +50 in a horizontal direction and from −50 to +50 in a vertical direction, while an area corresponding to a center part C1 ranges from −25 to +25 in the horizontal direction and from −25 to +25 in the vertical direction. It is also assumed that an area M1 corresponding to the lumen is a circle.

The imaging controller 302 determines that the central axis O of the capsule endoscope device 2 corresponds with the lumen orientation, namely the lumen is positioned in the center part C1 of the image, when the area M1 having low brightness is distributed in the center part C1 of an image W4 in the brightness distribution measured by the brightness distribution measurement unit 301, as illustrated in FIG. 8. On the other hand, the imaging controller 302 determines that the central axis O of the capsule endoscope device 2 does not correspond with the lumen orientation, namely the lumen is positioned outside the center part C1 of the image, when the area M1 having low brightness is distributed outside the center part C1 of the image W4 in the brightness distribution measured by the brightness distribution measurement unit 301.

The imaging controller 302 switches the frame rate of the imaging unit 23 on the basis of the brightness distribution of the image measured by the brightness distribution measurement unit 301, as described above. Therefore, according to the first embodiment, imaging can be performed at the frame rate corresponding to the condition of the capsule endoscope device 2 within the lumen of the subject 100 so that the information on the lumen can be acquired efficiently to save power. The capsule endoscope device 2 can be operated longer as a result.

Referring back to FIG. 4, processing performed in step S106 and on will be described.

The capsule endoscope device 2 ends the processing when an instruction signal instructing about termination of the operation of the capsule endoscope device 2 is externally input through the reception unit 29 to terminate the operation of the capsule endoscope device 2 in step S106 (step S106: Yes). On the other hand, the capsule endoscope device 2 returns to step S101 when the instruction signal instructing about termination of the operation of the capsule endoscope device 2 is not externally input through the reception unit 29, thereby not terminating the operation of the capsule endoscope device 2 (step S106: No).

According to the first embodiment of the present invention described above, the imaging controller 302 switches the frame rate of the imaging unit 23 on the basis of the brightness distribution of the image measured by the brightness distribution measurement unit 301, whereby the frame rate of the imaging unit 23 can be instantaneously switched with a simple configuration.

Moreover, according to the first embodiment of the present invention, the imaging controller 302 can efficiently acquire the information inside the lumen by switching the frame rate of the imaging unit 23 according to the condition of the capsule endoscope device 2 inside the lumen, whereby the capsule endoscope device 2 can be operated while saving power to be operated longer.

Figure 9:
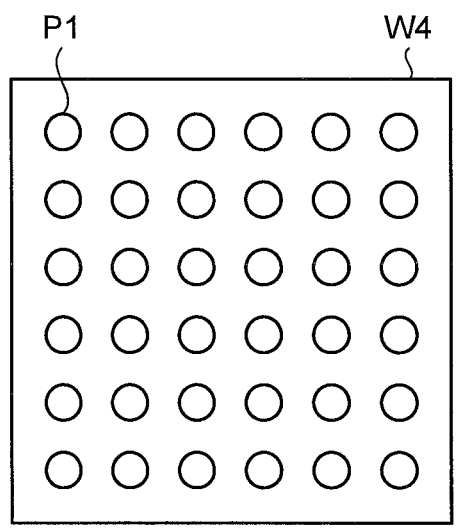
FIG. 9 is a diagram illustrating another example of a measurement method performed by a brightness distribution measurement unit of a capsule endoscope device according to a variation of the first embodiment of the present invention.

Note that while the brightness distribution measurement unit 301 in the first embodiment of the present invention uses one of the plurality of pixels forming the imaging unit 23, the brightness distribution of the image may instead be measured by using brightness in each of a plurality of dotted areas P1 in the image W4 as illustrated in FIG. 9 (multi-spot metering). This can reduce the computation performed by the brightness distribution measurement unit 301.

Second Embodiment

A second embodiment of the present invention will now be described. A capsule endoscope device of the second embodiment has a configuration similar to that of the capsule endoscope device 2 of the first embodiment but executes different processing therefrom. Therefore, the processing executed by the capsule endoscope device of the second embodiment will be described below. Note that a configuration similar to that of the capsule endoscope device 2 of the first embodiment will be assigned a reference sign identical to that assigned in the first embodiment to omit description of such configuration.

Processing Executed by Capsule Endoscope Device

Figure 10:
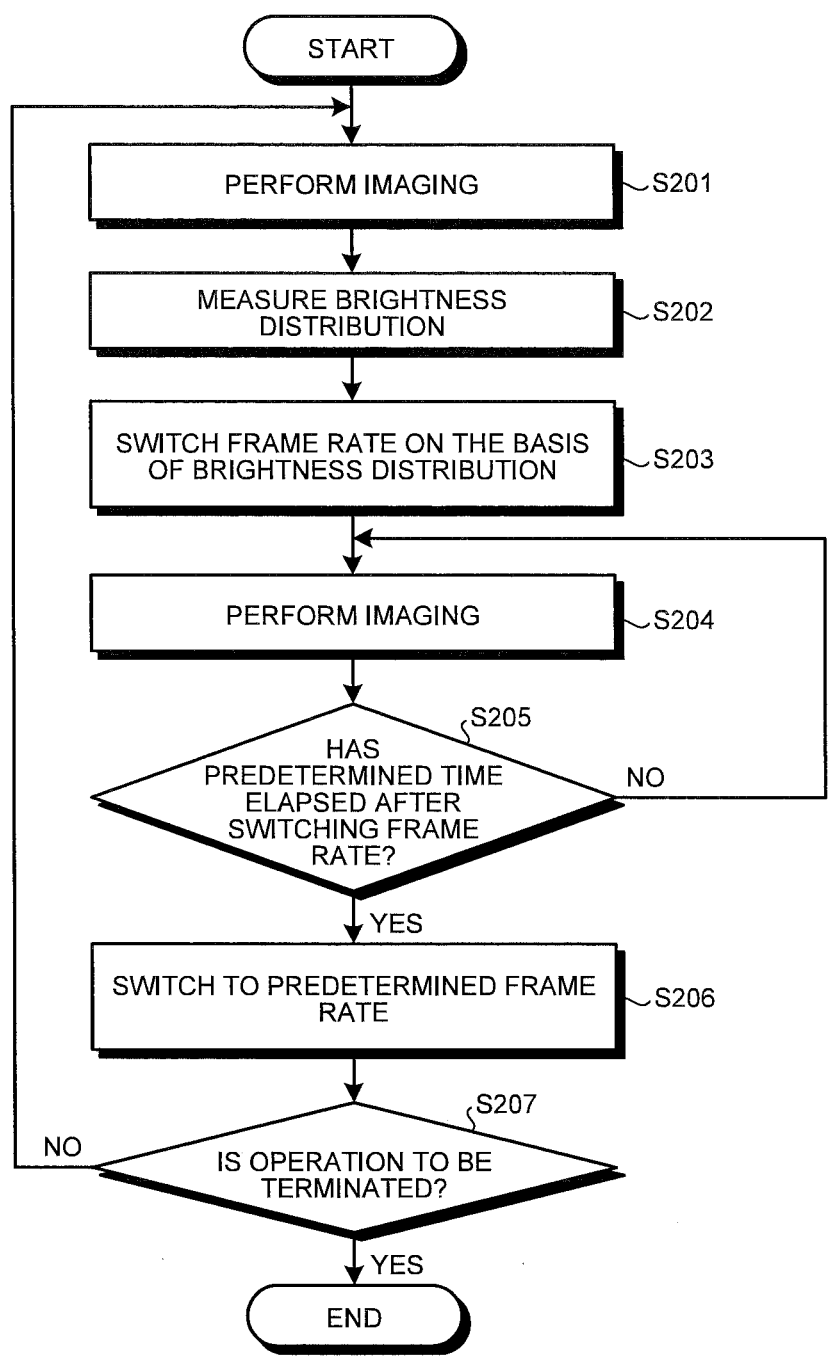
FIG. 10 is a flowchart illustrating an overview of processing executed by a capsule endoscope device according to a second embodiment of the present invention.

FIG. 10 is a flowchart illustrating an overview of the processing executed by a capsule endoscope device 2 according to the second embodiment.

Steps S201 and S202 in FIG. 10 correspond to steps S101 and S102 in FIG. 4, respectively.

In step S203, an imaging controller 302 switches a frame rate of an imaging unit 23 from a reference frame rate on the basis of a brightness distribution measured by a brightness distribution measurement unit 301. The imaging controller 302 for example switches the frame rate of the imaging unit 23 from 4 fps to 8 fps on the basis of the brightness distribution measured by the brightness distribution measurement unit 301.

Then, the imaging unit 23 captures an imaging area irradiated with illumination light by an illumination unit 24 (step S204).

The imaging controller 302 then determines, on the basis of time data input from a timer 28, whether or not a predetermined time has elapsed after switching the frame rate of the imaging unit 23 from the reference frame rate (step S205). The capsule endoscope device 2 proceeds to step S206 to be described when the imaging controller 302 determines that the predetermined time such as 30 seconds has elapsed after switching the frame rate of the imaging unit 23 from the reference frame rate (step S205: Yes). On the other hand, the capsule endoscope device 2 returns to step S204 when the imaging controller 302 determines that the predetermined time has not elapsed after switching the frame rate of the imaging unit 23 from the reference frame rate (step S205: No).

In step S206, the imaging controller 302 switches the frame rate of the imaging unit 23 to the reference frame rate. Specifically, the imaging controller 302 switches the frame rate of the imaging unit 23 from 8 fps to 4 fps, for example.

The capsule endoscope device 2 thereafter ends the processing when an instruction signal instructing about termination of an operation of the capsule endoscope device 2 is externally input through a reception unit 29 to terminate the operation of the capsule endoscope device 2 (step S207: Yes). On the other hand, the capsule endoscope device 2 returns to step S201 when the instruction signal instructing about termination of the operation of the capsule endoscope device 2 is not externally input through the reception unit 29, thereby not terminating the operation of the capsule endoscope device 2 (step S207: No).

According to the second embodiment of the present invention described above, the imaging controller 302 switches the frame rate of the imaging unit 23 on the basis of the brightness distribution of the image measured by the brightness distribution measurement unit 301, whereby the frame rate of the imaging unit 23 can be instantaneously switched with a simple configuration.

Moreover, according to the second embodiment of the present invention, the imaging controller 302 can efficiently acquire information inside a lumen by switching the frame rate of the imaging unit 23 to the reference frame rate when determining that the predetermined time has elapsed after switching the frame rate of the imaging unit 23 from the reference frame rate on the basis of the time data input from the timer 28, whereby the capsule endoscope device 2 can be operated while saving power.

Third Embodiment

A third embodiment of the present invention will now be described. A capsule endoscope device of the third embodiment has a configuration different from that of the capsule endoscope device 2 of the first embodiment. Specifically, the capsule endoscope device of the present embodiment includes two imaging units capturing imaging areas that are different from each other. There will thus be described the configuration of the capsule endoscope device of the third embodiment, followed by description of processing executed by the capsule endoscope device of the third embodiment. Note that a configuration identical to that of the capsule endoscope device 2 of the first embodiment will be assigned a reference sign identical to that assigned in the first embodiment to omit description of such configuration.

Configuration of Capsule Endoscope Device

Figure 11:
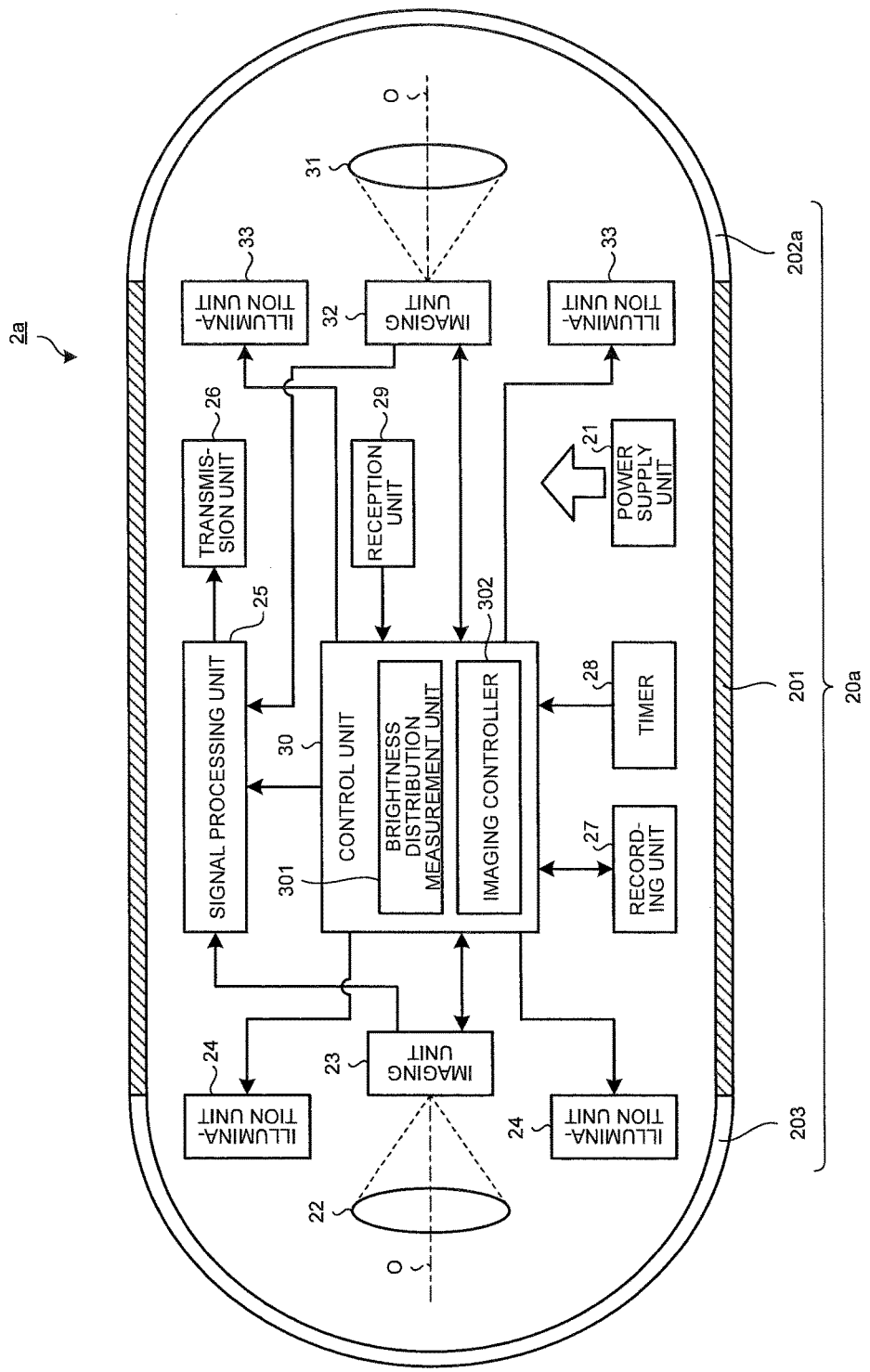
FIG. 11 is a block diagram illustrating a functional configuration of a capsule endoscope device according to a third embodiment of the present invention.

FIG. 11 is a block diagram illustrating a functional configuration of the capsule endoscope device according to the third embodiment.

A capsule endoscope device 2a illustrated in FIG. 11 includes an optical system 31, an imaging unit 32, and an illumination unit 33 in addition to the configuration of the capsule endoscope device 2 according to the first embodiment. The capsule endoscope device 2a further includes a casing 20a in place of the casing 20 included in the capsule endoscope device 2 of the first embodiment.

The casing 20a is capsule-shaped and sized to be easily inserted into a subject 100. The casing 20a has a cylindrical portion 201, and dome-shaped dome portions 202a and 203 that close openings at both ends of the cylindrical portion 201. The dome portion 202a is formed by using an optical member that can transmit light in a predetermined wavelength band such as visible light. The casing 20a is arranged along a central axis of the capsule endoscope device 2a in a longitudinal direction and accommodates an imaging unit 23 and the imaging unit 32 capturing imaging areas that are different from each other.

The optical system 31 has a configuration similar to that of the optical system 22 described above, and forms a subject image by condensing reflected light of illumination light radiated by the illumination unit 33 onto an imaging surface of the imaging unit 32. The optical system 31 is arranged in the casing 20a such that an optical axis of the system corresponds with a central axis O of the casing 20a in the longitudinal direction.

The imaging unit 32 has a configuration similar to that of the imaging unit 23 described above and, under control of the control unit 30, generates image data of the subject 100 by performing photoelectric conversion on the subject image formed on a light receiving surface by the optical system 31. Moreover, the imaging unit 32 is arranged in the casing 20a such that the light receiving surface of the imaging unit 32 is orthogonal to the central axis O. Note that in the third embodiment, the imaging unit 23 functions as a first imaging unit while the imaging unit 32 functions as a second imaging unit. Accordingly, in the following description, the imaging unit 23 will be referred to as a first imaging unit 23 while the imaging unit 32 will be referred to as a second imaging unit 32.

The illumination unit 33 has a configuration similar to that of the illumination unit 24 described above and, under control of the control unit 30, radiates the illumination light toward a subject within an imaging field of the imaging unit 32 in synchronization with a frame rate of the imaging unit 32.

Processing Executed by Capsule Endoscope Device

There will now be described the processing executed by the capsule endoscope device 2a. FIG. 12 is a flowchart illustrating an overview of the processing executed by the capsule endoscope device 2a.

As illustrated in FIG. 12, an imaging controller 302 first causes each of the illumination units 24 and 33 to radiate the illumination light and causes the first imaging unit 23 and the second imaging unit 32 to capture imaging areas irradiated with the illumination light by the illumination units 24 and 33 (step S301).

A brightness distribution measurement unit 301 then measures a brightness distribution in each of two images corresponding to two image data generated by the first imaging unit 23 and the second imaging unit 32 (step S302).

After that, the imaging controller 302 determines whether or not an area having brightness lower than a predetermined value is distributed at the center of the image in the brightness distribution measured by the brightness distribution measurement unit 301 in each of the two images generated by the first imaging unit 23 and the second imaging unit 32 (step S303). The imaging controller 302 switches a frame rate of each of the first imaging unit 23 and the second imaging unit 32 to a higher frame rate higher than a reference frame rate (step S304) when the imaging controller 302 determines that the area having the brightness lower than the predetermined value is distributed at the center of the image in the brightness distribution measured by the brightness distribution measurement unit 301 in each of the two images generated by the first imaging unit 23 and the second imaging unit 32 (step S303: Yes). Specifically, the imaging controller 302 switches the frame rate of each of the first imaging unit 23 and the second imaging unit 32 from the reference frame rate being 4 fps to a higher frame rate being 16 fps (from 4 fps to 16 fps). Following step S304, the capsule endoscope device 2a proceeds to step S306 to be described.

The imaging controller 302 switches the frame rate of each of the first imaging unit 23 and the second imaging unit 32 to a lower frame rate lower than the reference frame rate (step S305) when the imaging controller 302 determines in step S303 that the area having the brightness lower than the predetermined value is not distributed at the center of the image in the brightness distribution measured by the brightness distribution measurement unit 301 in each of the two images generated by the first imaging unit 23 and the second imaging unit 32 (step S303: No). Specifically, the imaging controller 302 switches the frame rate of each of the first imaging unit 23 and the second imaging unit 32 from the reference frame rate being 4 fps to a lower frame rate being 2 fps (from 4 fps to 2 fps). Following step S305, the capsule endoscope device 2a proceeds to step S306 to be described.

There will now be described a condition in which the imaging controller 302 switches the frame rate of the first imaging unit 23 and the second imaging unit 32 on the basis of the brightness distribution measured by the brightness distribution measurement unit 301 in the two images generated by the first imaging unit 23 and the second imaging unit 32.

Figure 13A:
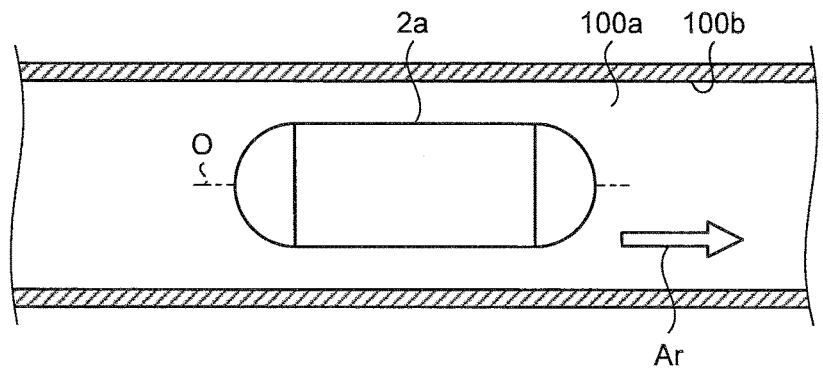
FIG. 13A is a diagram illustrating an example of a state of the capsule endoscope device inside a lumen of a subject.
Figure 13B:
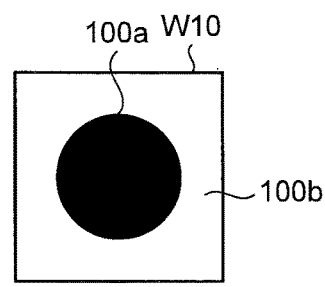
FIG. 13B is a diagram illustrating a first image corresponding to first image data captured by a first imaging unit under the condition illustrated in FIG. 13A.
Figure 13C:
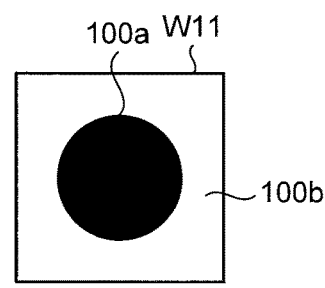
FIG. 13C is a diagram illustrating a second image corresponding to second image data captured by a second imaging unit under the condition illustrated in FIG. 13A.
Figure 14A:
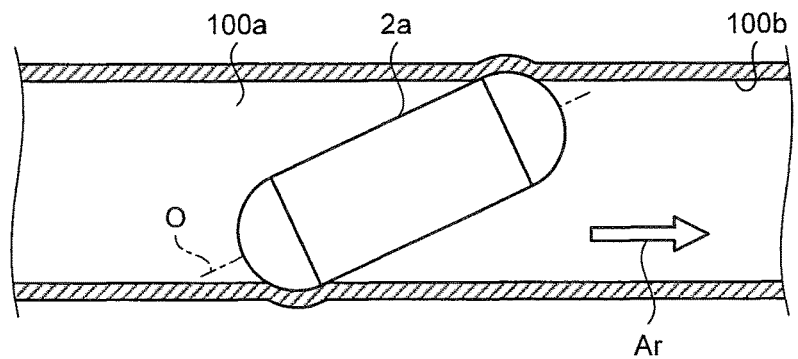
FIG. 14A is a diagram illustrating an example of another state of the capsule endoscope device inside the lumen of the subject.
Figure 14B:
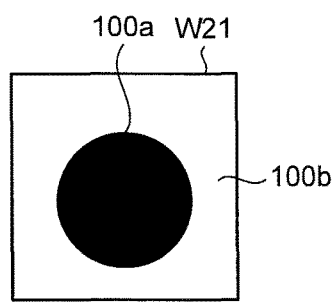
FIG. 14B is a diagram illustrating a first image corresponding to first image data captured by a first imaging unit under the condition illustrated in FIG. 14A.
Figure 14C:
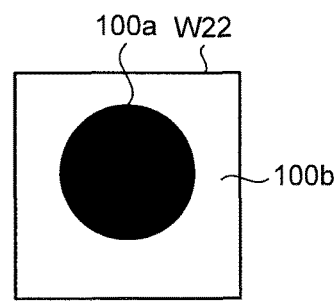
FIG. 14C is a diagram illustrating a second image corresponding to second image data captured by a second imaging unit under the condition illustrated in FIG. 14A.
Figure 15A:
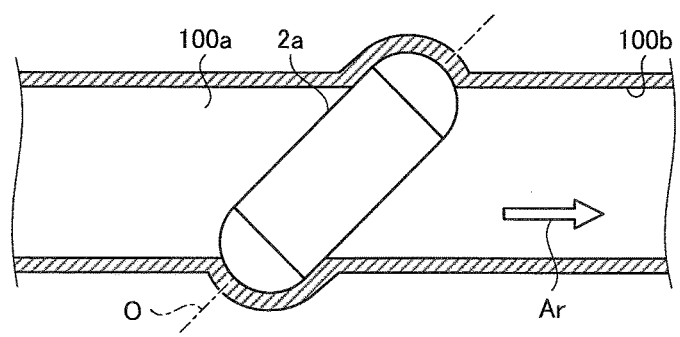
FIG. 15A is a diagram illustrating an example of another state of the capsule endoscope device inside the lumen of the subject.
Figure 15B:
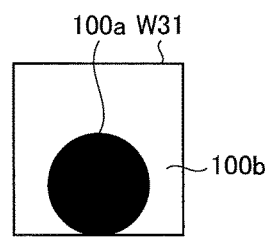
FIG. 15B is a diagram illustrating a first image corresponding to first image data captured by a first imaging unit under the condition illustrated in FIG. 15A.
Figure 15C:
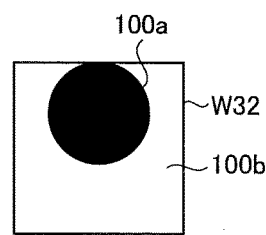
FIG. 15C is a diagram illustrating a second image corresponding to second image data captured by a second imaging unit under the condition illustrated in FIG. 15A.

FIG. 13A is a diagram illustrating an example of a state (first state) of the capsule endoscope device 2a inside a lumen of the subject 100. FIG. 13B is a diagram illustrating a first image corresponding to first image data captured by the first imaging unit 23 under the condition illustrated in FIG. 13A. FIG. 13C is a diagram illustrating a second image corresponding to second image data captured by the second imaging unit 32 under the condition illustrated in FIG. 13A. FIG. 14A is a diagram illustrating an example of another state (second state) of the capsule endoscope device 2a inside the lumen of the subject 100. FIG. 14B is a diagram illustrating a first image corresponding to first image data captured by the first imaging unit 23 under the condition illustrated in FIG. 14A. FIG. 14C is a diagram illustrating a second image corresponding to second image data captured by the second imaging unit 32 under the condition illustrated in FIG. 14A. FIG. 15A is a diagram illustrating an example of another state (third state) of the capsule endoscope device 2a inside the lumen of the subject 100. FIG. 15B is a diagram illustrating a first image corresponding to first image data captured by the first imaging unit 23 under the condition illustrated in FIG. 15A. FIG. 15C is a diagram illustrating a second image corresponding to second image data captured by the second imaging unit 32 under the condition illustrated in FIG. 15A.

The capsule endoscope device 2a includes a lumen 100a at the center of each of a first image W10 and a second image W11 (refer to FIGS. 13B and 13C) generated by the first imaging unit 23 and the second imaging unit 32, respectively, when the central axis O of the capsule endoscope device 2a corresponds with a lumen orientation (arrow Ar) in the subject 100 as illustrated in FIG. 13A.

On the other hand, the capsule endoscope device 2a images the lumen 100a at a position deviating from the center of each of a first image W21 and a second image W22 or a first image W31 and a second image W32 generated by the first imaging unit 23 and the second imaging unit 32, respectively, when the central axis O of the capsule endoscope device 2a does not correspond with the lumen orientation (arrow Ar) in the subject 100 as illustrated in FIGS. 14A and 15A, such as when an optical axis of either one of the first imaging unit 23 and the second imaging unit 32 deviates from the lumen orientation of the subject.

Now, the imaging controller 302 in the third embodiment switches the frame rate of each of the first imaging unit 23 and the second imaging unit 32 to a higher frame rate higher than the reference frame rate (from 4 fps to 16 fps) when the area having the brightness lower than the predetermined value is determined to be distributed at the center of each of the two images on the basis of the brightness distribution measured by the brightness distribution measurement unit 301 in each of the two images generated by the first imaging unit 23 and the second imaging unit 32. On the other hand, the imaging controller 302 switches the frame rate of each of the first imaging unit 23 and the second imaging unit 32 to a lower frame rate lower than the reference frame rate (from 4 fps to 2 fps) when the area having the brightness lower than the predetermined value is distributed outside the center of the image in at least one of the two images generated by the first imaging unit 23 and the second imaging unit 32. As a result, there can be determined accurately whether or not the central axis O of the capsule endoscope device 2a corresponds with the lumen orientation in the subject 100.

Referring back to FIG. 12, processing performed in step S306 and on will be described.

The capsule endoscope device 2a ends the processing when an instruction signal instructing about termination of the operation of the capsule endoscope device 2a is externally input through a reception unit 29 to terminate the operation of the capsule endoscope device 2a in step S306 (step S306: Yes). On the other hand, the capsule endoscope device 2a returns to step S301 when the instruction signal instructing about termination of the operation of the capsule endoscope device 2a is not externally input through the reception unit 29, thereby not terminating the operation of the capsule endoscope device 2a (step S306: No).

According to the third embodiment described above, the imaging controller 302 switches the frame rate of the first imaging unit 23 and the second imaging unit 32 on the basis of the brightness distribution of the first and second images measured by the brightness distribution measurement unit 301, whereby the frame rate can be instantaneously switched with a simple configuration.

Moreover, according to the third embodiment of the present invention, the imaging controller 302 can efficiently acquire the information inside the lumen of the subject 100 by switching the frame rate of the first imaging unit 23 and the second imaging unit 32 according to the condition of the capsule endoscope device 2a inside the lumen, whereby the capsule endoscope device 2a can be operated while saving power to be operated longer.

Note that while the imaging controller 302 in the third embodiment of the present invention switches the frame rate of each of the first imaging unit 23 and the second imaging unit 32 on the basis of the brightness distribution in the first and second images measured by the brightness distribution measurement unit 301, it may also be adapted to switch the frame rate of each of the first imaging unit 23 and the second imaging unit 32 to the reference frame rate (from 16 fps to 4 fps, for example) when a predetermined time elapses after switching the frame rate of each of the first imaging unit 23 and the second imaging unit 32. The information inside the lumen can thus be acquired efficiently.

Moreover, while the brightness distribution measurement unit 301 in the third embodiment of the present invention measures the brightness distribution by using one predetermined type of pixel in each of the first and second images generated by the first imaging unit 23 and the second imaging unit 32, the brightness distribution may also be measured by using brightness in a plurality of dotted areas P1 in each of the first and second images (refer to FIG. 9). This can reduce the computation performed by the brightness distribution measurement unit 301.

Furthermore, while the imaging controller 302 in the third embodiment of the present invention switches the frame rate of each of the first imaging unit 23 and the second imaging unit 32 together, the frame rates of the first imaging unit 23 and the second imaging unit 32 need not be matched where, for example, the frame rate of the first imaging unit 23 alone may be switched to a higher frame rate.

According to some embodiments, the frame rate of the imaging unit can be switched instantaneously with a simple configuration.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule endoscope device configured to be inserted into a subject, the capsule endoscope device comprising:
 a first image sensor configured to capture a first imaging area inside of the subject and to generate a first image of the inside of the subject; and
 a processor comprising hardware, wherein the processor is configured to:
  measure a brightness distribution in the first image generated by the first image sensor;
  switch a frame rate of the first image sensor to a frame rate higher than a reference frame rate when an area having brightness lower than a predetermined value is distributed at a center of the first image in the brightness distribution in the first image measured; and
  switch the frame rate of the first image sensor to a frame rate lower than the reference frame rate when the area having the brightness lower than the predetermined value is not distributed at the center of the first image in the brightness distribution in the first image measured and the area having the brightness lower than the predetermined value is distributed outside the center of the first image in the brightness distribution in the first image measured.

2. The capsule endoscope device according to claim 1, further comprising:
 a second image sensor configured to capture a second imaging area inside of the subject and to generate a second image of the inside of the subject,
 wherein the first image sensor and the second image sensor are arranged along a central axis of the capsule endoscope device in a longitudinal direction, wherein the first image sensor and the second image sensor are configured such that the first imaging area is different from the second imaging area; and wherein the processor is configured to:
  measure a brightness distribution in the second image generated by the second image sensor;
  switch the frame rate of the first image sensor and a frame rate of the second image sensor to the frame rate higher than the reference frame rate when:
    the area having brightness lower than the predetermined value is distributed at the center of the first image in the brightness distribution in the first image measured, and
    an area having brightness lower than the predetermined value is distributed at a center of the second image in the brightness distribution in the second image measured; and
  switch the frame rate of the first image sensor and the frame rate of the second image sensor to the frame rate lower than the reference frame rate when:
    the area having brightness lower than the predetermined value is not distributed at the center of the first image in the brightness distribution in the first image measured,
    the area having brightness lower than the predetermined value is not distributed at the center of the second image in the brightness distribution in the second image measured,
    the area having the brightness lower than the predetermined value is distributed outside the center of the first image in the brightness distribution in the first image measured, and
    the area having the brightness lower than the predetermined value is distributed outside the center of the second image in the brightness distribution in the second image measured.

3. The capsule endoscope device according to claim 2, wherein the processor is configured to measure the brightness distribution in the first image measured and the brightness distribution in the second image measured by using brightness in a plurality of dotted areas in each of the first image and the second image.

4. The capsule endoscope device according to claim 1, wherein the processor is configured to switch the frame rate of the first image sensor to the reference frame rate when a predetermined time elapses after switching the frame rate of the first image sensor.

* * * * *